United States Patent
Ning et al.

(10) Patent No.: US 9,983,137 B2
(45) Date of Patent: May 29, 2018

(54) SAFETY PROTECTION DEVICE AND RAMAN SPECTROSCOPY DETECTION SYSTEM FOR RAMAN SPECTROSCOPY DETECTION

(71) Applicant: NUCTECH COMPANY LIMITED, Beijing (CN)

(72) Inventors: Yanshi Ning, Beijing (CN); Li Zhang, Beijing (CN); Hongqiu Wang, Beijing (CN); Yumin Yi, Beijing (CN); Shixin Zhang, Beijing (CN)

(73) Assignee: Nuctech Company Limited, Beijing (CN)

( * ) Notice: Subject to any disclaimer, the term of this patent is extended or adjusted under 35 U.S.C. 154(b) by 54 days.

(21) Appl. No.: 15/271,297

(22) Filed: Sep. 21, 2016

(65) Prior Publication Data
US 2017/0184503 A1 Jun. 29, 2017

(30) Foreign Application Priority Data
Dec. 23, 2015 (CN) .......................... 2015 1 0976225

(51) Int. Cl.
*G01N 21/65* (2006.01)
*G01N 33/00* (2006.01)

(52) U.S. Cl.
CPC ......... *G01N 21/65* (2013.01); *G01N 33/0057* (2013.01); *G01N 2021/651* (2013.01);
(Continued)

(58) Field of Classification Search
CPC ............. G01N 2021/656; G01N 21/01; G01N 2021/0106; G01N 2021/0112;
(Continued)

(56) References Cited

U.S. PATENT DOCUMENTS 5,495,747 A * 3/1996 Herman ................. G01N 27/16
73/23.2
5,978,534 A 11/1999 O'Rourke et al.
(Continued)

FOREIGN PATENT DOCUMENTS

CN 101915757 A 12/2010
CN 102023149 A 4/2011
(Continued)

OTHER PUBLICATIONS

Grisch et al., "Real time diagnostics of detonation products from lead azide using coherent anti-Stokes Raman scattering", Appl. Phys. Lett., vol. 59, No. 27, Dec. 30, 1991, pp. 3516-3518.
(Continued)

*Primary Examiner* — Michael P Lapage
(74) *Attorney, Agent, or Firm* — Morgan, Lewis & Bockius LLP

(57) ABSTRACT

Embodiments of the present disclosure provide a safety protection device for Raman spectroscopy detection and a Raman spectroscopy detection system including the safety protection device. The safety protection device includes: a detection cavity including a cavity body, the cavity body having an opening end through which a sample to be detected is allowed to be placed into the detection cavity; and a cover configured to cover and engage the opening end so as to form, together with the detection cavity, an explosion proof container defining a space for receiving the sample to be detected, the detection cavity further includes a detection opening formed in the cavity body such that a Raman detection probe is allowed to be inserted into the space through the detection opening so as to detect the sample.

18 Claims, 6 Drawing Sheets

(52) U.S. Cl.
CPC .............. *G01N 2201/022* (2013.01); *G01N 2201/0236* (2013.01)

(58) Field of Classification Search
CPC .. G01N 33/0057; G01N 33/22; G01N 33/227; A61B 5/0075
See application file for complete search history.

(56) References Cited

U.S. PATENT DOCUMENTS

| | | | | |
|---|---|---|---|---|
| 7,385,692 | B1* | 6/2008 | Nguyen | G01J 3/02 356/301 |
| 9,575,046 | B1* | 2/2017 | Laquidara | G01N 33/227 |
| 2007/0102639 | A1* | 5/2007 | Cutler | G01N 21/3504 250/339.13 |
| 2008/0308733 | A1* | 12/2008 | Doncaster | G01N 21/0303 250/343 |
| 2014/0118732 | A1* | 5/2014 | Ayers | G01N 21/65 356/301 |
| 2016/0091418 | A1* | 3/2016 | Schachinger | G01N 21/31 356/437 |
| 2016/0349172 | A1* | 12/2016 | Houghton | G01N 33/227 |

FOREIGN PATENT DOCUMENTS

| | | |
|---|---|---|
| CN | 104458697 A | 3/2015 |
| CN | 104931477 A | 9/2015 |
| CN | 205262968 U | 5/2016 |
| JP | H09-203669 A | 8/1997 |

OTHER PUBLICATIONS

Miron et al., "Multiple charge reaction cell for studies of primary explosives", Review of Scientific Instruments, vol. 60, No. 1, Jan. 1989, pp. 132-134.
First Office Action dated Aug. 16, 2017, for corresponding Chinese Patent Application No. 201510976225.5.

* cited by examiner

SAFETY PROTECTION DEVICE AND RAMAN SPECTROSCOPY DETECTION SYSTEM FOR RAMAN SPECTROSCOPY DETECTION

CROSS-REFERENCE TO RELATED APPLICATION

This application claims the benefit of the Chinese Patent Application No. 201510976225.5 tilted "SAFETY PROTECTION DEVICE AND RAMAN SPECTROSCOPY DETECTION SYSTEM FOR RAMAN SPECTROSCOPY DETECTION" filed on Dec. 23, 2015 in the State Intellectual Property Office of China, the whole disclosure of which is incorporated herein by reference.

BACKGROUND OF THE INVENTION

Field of the Invention

Embodiments of the present disclosure generally relate to the field of safety detection technologies, and particularly, to a safety protection device for Raman spectroscopy detection, and a Raman spectroscopy detection system comprising the safety protection device, for detecting inflammable, explosive dangerous substances.

Description of the Related Art

Raman spectrum is a molecular vibration spectrum, which may be indicative of fingerprint features of a molecule and used for substance detection. In a Raman spectroscopy detection technology, a substance is detected and identified through a Raman spectrum generated due to a Raman scattering effect of exciting light by the substance. The Raman spectroscopy detection technologies have been widely applied in fields such as liquid safety detection, jewelry detection, explosive detection, drug detection, medicine detection or the like.

Currently, Raman laser spectroscopy technologies for detecting dangerous substances includes advantages such as simple and quick operation, no damage and the like, and are performed such that a laser beam may be irradiated onto a sample by an optic fiber probe, and a Raman spectrum of the sample is determine by collecting a Raman scattering spectrum. A common Raman laser is 785 nm near infrared laser, which has a relatively concentrated energy distribution at its focus point under a certain power and for an operation time period, which will easily cause deflagration and even explosion of inflammable, explosive dangerous substances such as black powder or the like, thereby resulting in damage to a detection personnel and onsite detection operation. An existing Raman detection instrument is not equipped with any protection device when detecting dangerous substances, and may meet safety testing requirements through remote location of the personnel or delay measurement, which would bring about a lot of troubles in actual field use.

SUMMARY

The present invention has been made to overcome or alleviate at least one aspect of the above mentioned problems and disadvantages.

According to an aspect of the present disclosure, there is provided a safety protection device for Raman spectroscopy detection, comprising: a detection cavity comprising a cavity body, the cavity body having an opening end through which a sample to be detected is allowed to be placed into the detection cavity; and a cover configured to cover and engage the opening end so as to form, together with the detection cavity, an explosion proof container defining a space for receiving the sample to be detected, wherein the detection cavity comprises a detection opening formed in the cavity body such that a Raman detection probe is allowed to be inserted into the space through the detection opening so as to detect the sample.

In an embodiment, the above safety protection device may further comprise a sample holder which is provided within the detection cavity and on which the sample to be detected is placed.

In an embodiment, the sample holder may comprise: a base mounted within the detection cavity and having a detection region on which the sample to be detected is to be placed; and a shielding plate connected with the base, the shielding plate being configured such that the detection opening and the detection region are located on opposite sides of the shielding plate and having an open pore aligned with the detection opening so that the Raman detection probe is allowed to pass through the detection opening and the open pore that are aligned with each other so as to be located near the detection region.

In an embodiment, the above safety protection device may further comprise a probe limiting block located within the detection cavity and configured to guide and hold the Raman detection probe passing through the detection opening to be located near the detection region.

In an embodiment, the probe limiting block may comprise a limiting hole configured to be aligned with the detection opening and the open pore so as to receive the Raman detection probe.

In an embodiment, the probe limiting block may be positioned within the detection cavity between a side wall of the detection cavity in which the detection opening is formed and the shielding plate.

In an embodiment, the detection cavity and/or cover may further comprise a pressure relief opening in communication with the space.

In an embodiment, the detection cavity may further comprise a notched engagement ring located at the opening end and formed with a first engagement structure, and the cover may be formed with a second engagement structure configured to be engaged with and locked with respect to the first engagement structure.

In an embodiment, the first engagement structure may comprise a plurality of notch engagement structures circumferentially spaced apart from each other, and the second engagement structure comprises a plurality of engagement legs each configured to engage a corresponding one of the notch engagement structures in a snap fit connection such that the cover is detachably engaged and locked to detection cavity.

According to another aspect of the present disclosure, there is provided a Raman spectroscopy detection system, comprising: the safety protection device as described above; and a detection device, the detection device comprising the Raman detection probe, which is configured to be partially inserted into the space through the detection opening and detect the sample within space so as to obtain a Raman spectrum of the sample.

Other features and advantages of the present disclosure will become more apparent by describing in detail exemplary embodiments thereof with reference to the accompanying drawings, which may help comprehensive understanding of the present disclosure.

BRIEF DESCRIPTION OF THE DRAWINGS

Features and advantages of the present disclosure can be understood more clearly with reference to the accompanying drawings, which are illustrative and should not be construed as a limit to the invention. In the drawings.

DETAINED DESCRIPTION OF PREFERRED EMBODIMENTS OF THE INVENTION

Figure 1A:
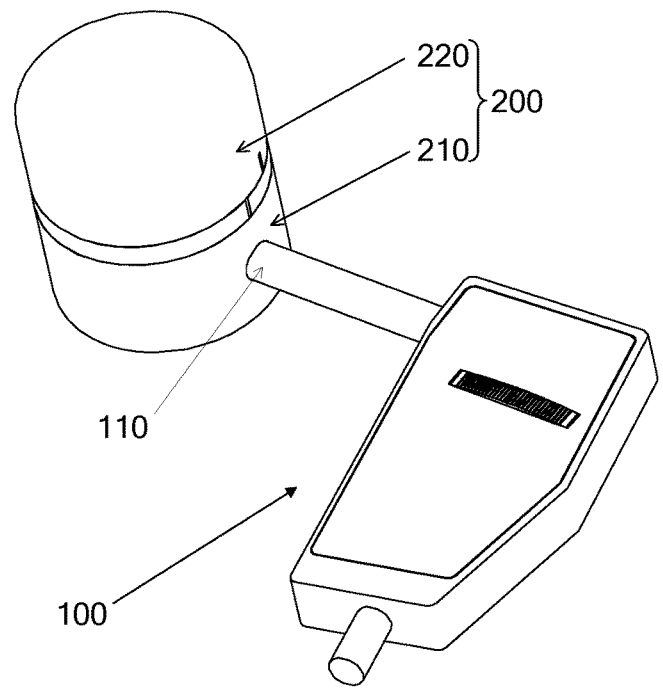
FIGS. 1A and 1B are diagrams schematically showing a Raman spectroscopy detection system comprising a safety protection device according to an exemplary embodiment of the present disclosure, with a cover of the safety protection device being removed from FIG. 1B.

Technical solutions of the present disclosure will be further described in detail in combination with exemplary embodiments with reference to the attached drawings. In the description, the same or like reference numbers refer to the same or like elements. The following description of exemplary embodiments of the present disclosure made with reference to the attached drawings is intended to illustrate the general inventive concepts of the present disclosure, and should not be interpreted as being limitative to the present disclosure.

Further, in the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

According to a general concept of the present disclosure, there is provided a safety protection device for Raman spectroscopy detection, comprising a detection cavity and a cover, the cover is configured to cover the detection cavity such that the cover and the detection cavity together form an explosion proof container defining a space for receiving a sample to be detected, and a detection instrument, such as a Raman detection probe, is allowed to detect the sample within the space. Thereby, even if dangerous conditions such as deflagration and explosion of inflammable, explosive dangerous substances occur during detection, these dangerous conditions can be restricted within the explosion proof container and be effectively prevented from causing damage to a detection personnel or onsite detection operation.

Figure 1B:
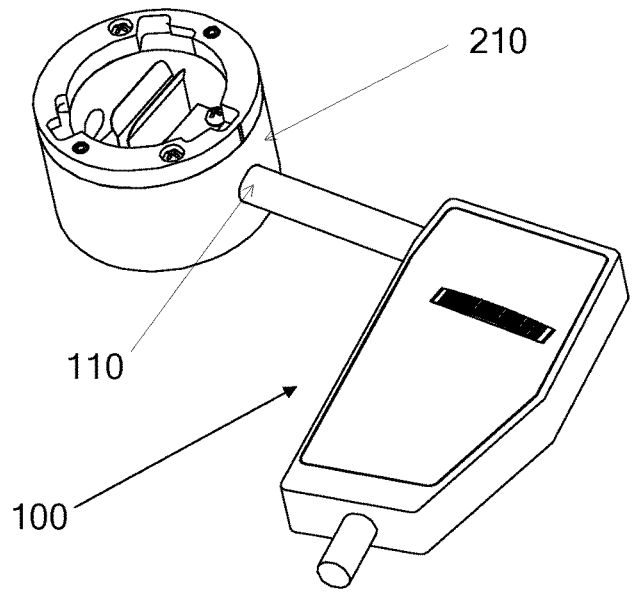

FIGS. 1A and 1B schematically show an exemplary Raman spectroscopy detection system for detecting a sample to be detected by using the safety protection device of embodiments of the present disclosure. As shown in the figures, the Raman spectroscopy detection system comprises a detection device 100 and a safety protection device 200 configured as an explosion proof container, which defines therein a space for receiving or placing a sample to be detected such as solid powder. The detection device 100 may comprise a Raman detection probe 110, which may be partially placed within the space of the safety protection device 200 to perform detection of the sample within the space, thereby obtaining a Raman spectrum of the sample. Exemplarily, the Raman detection probe 110 may irradiate a light beam such as a laser beam onto the sample to be detected and collect a Raman scattering spectrum of the sample so as to determine the Raman spectrum of the sample.

In an example, the safety protection device 200 may include a split type configuration comprising a detection cavity 210 and a cover 220, which are engaged with each other so as to form the explosion proof container defining the space for receiving the sample to be detected. The split type safety protection device may be easily carried and assembled on site and facilitate placement of the sample to be detected. It will be understood, however, that the safety protection device 200 may be configured in an integral configuration provided with an opening through which the sample to be detected is allowed to be placed within the space. In addition, the safety protection device, as a whole, may has a shape in form of a cylinder, a sphere, a cuboid or others, which will not be limited in the present disclosure. In an embodiment shown in FIG. 2A, the detection cavity 210 comprises a cavity body 22 having an opening end, such that the sample to be detected may be allowed to be placed into the detection cavity through the opening end or other opening. The cover 220 is configured to cover the opening end of the cavity body 211 and to be detachably engaged with the detection cavity 210, for example, be locked to the detection cavity 210, so as to form, together with the detection cavity 210, the explosion proof container defining the space for receiving the sample to be detected.

Figure 2A:
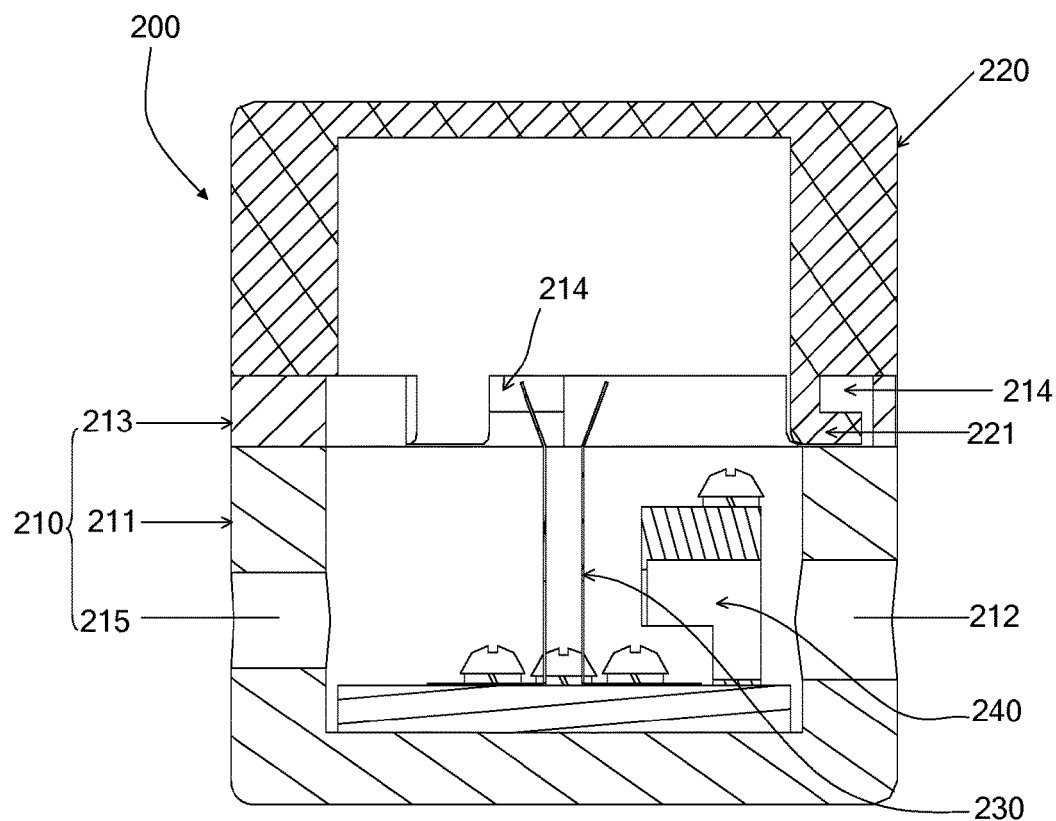
FIG. 2A is a cross sectional view schematically showing a safety protection device according to an exemplary embodiment of the present disclosure.
Figure 4:
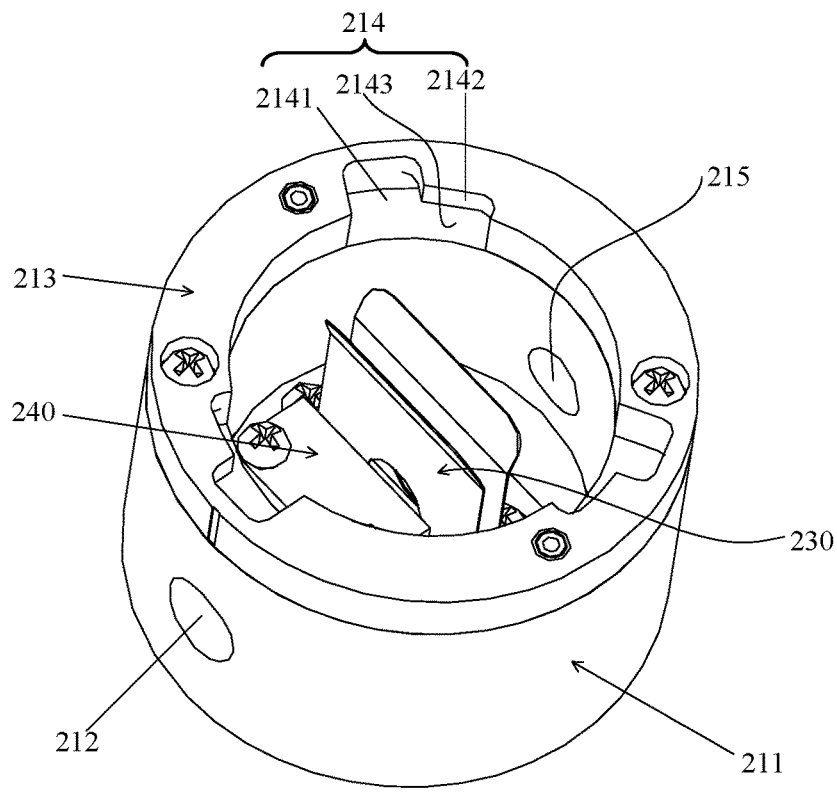
FIG. 4 is a perspective view schematically showing a detection cavity according to an exemplary embodiment of the present disclosure.

As shown in FIG. 2A and FIG. 4, the detection cavity 210 may further comprise a detection opening 212 formed in the cavity body 211, for example, in a side wall of the cavity body 211, such that the Raman detection probe 110 is allowed to be partially inserted into the space of the safety protection device 200 through the detection opening 212 so as to detect the sample within the space.

Figure 2B:
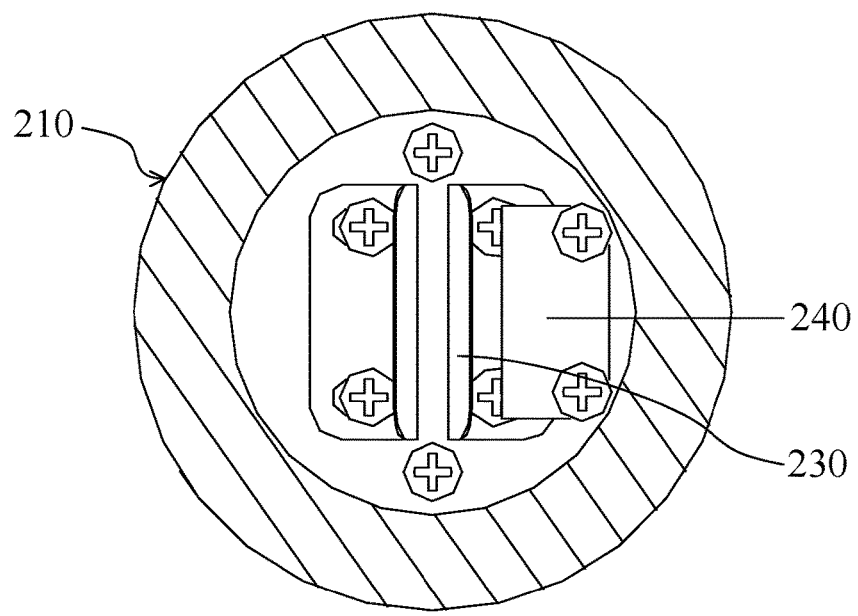
FIG. 2B is a top view schematically showing the safety protection device shown in FIG. 2A, with the cover being removed.
Figure 3:
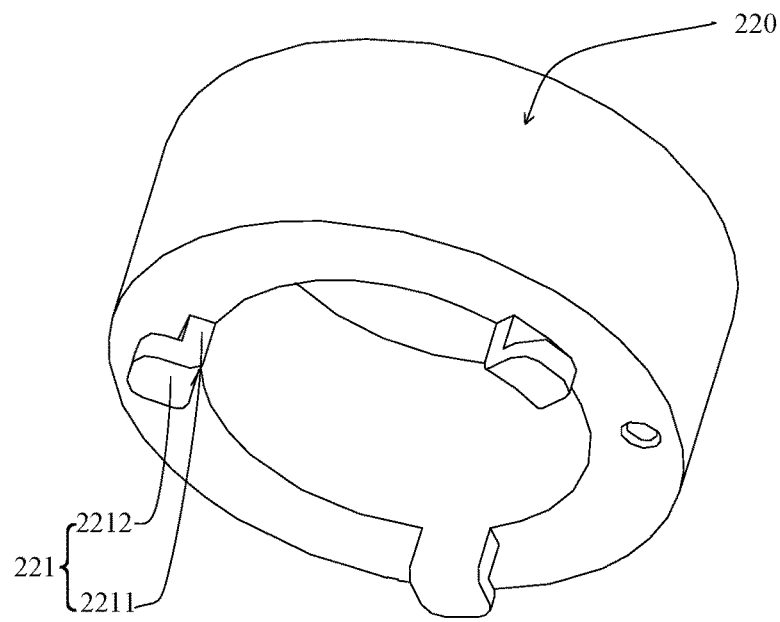
FIG. 3 is a perspective view schematically showing a cover according to an exemplary embodiment of the present disclosure.
Figure 6:
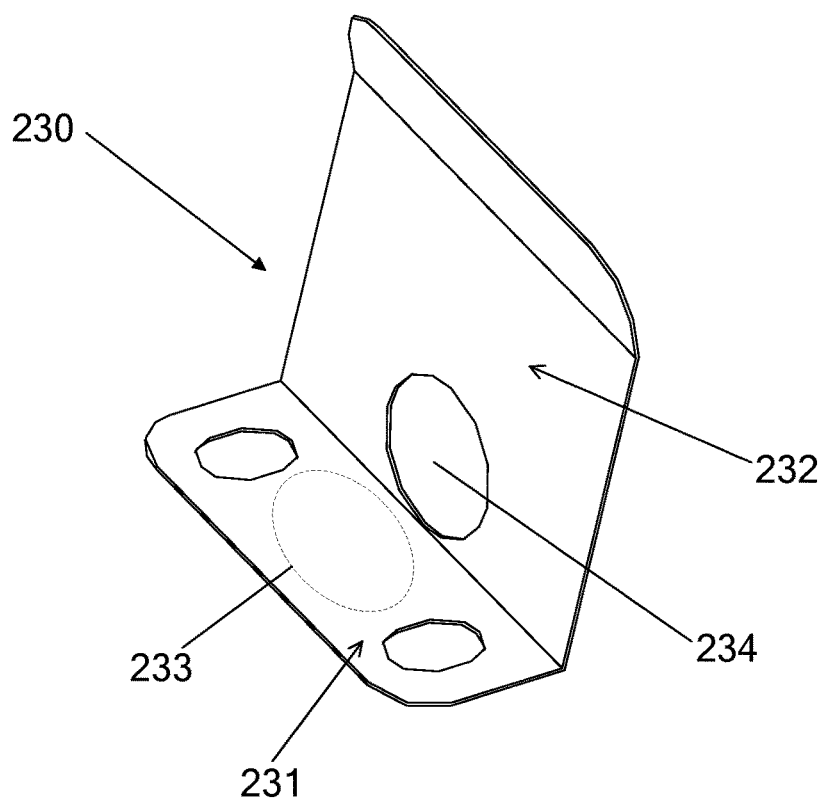
FIG. 6 is a perspective view schematically showing a sample holder according to an exemplary embodiment of the present disclosure.

A sample holder 230 may be provided or mounted within the detection cavity 210, as shown in FIGS. 2A, 2B and 4, and the sample to be detected may be placed on the sample holder 230. The sample holder may be in form of a spring clip, a notched metal block or the like. FIG. 6 shows an example of the sample holder 230, which may be, as a whole, in a substantially L-shape, and comprises a base 231 mounted within the detection cavity 210 and a shielding plate 232 connected with the base 231. The base 231 may have a detection region 233 on which the sample to be detected is to be placed to indicate the detection personnel to place the sample to be detected in position. The base 231 may be detachably or non-detachably fixed or mounted within the detection cavity 210 via various means, for example, a bolt.

As shown in FIGS. 2A and 4, the shielding plate 232 is configured such that the detection opening 212 and the detection region 233 are located on opposite sides of the shielding plate, so as to reduce escaping of inflammable, explosive dangerous substances or gases from the safety protection device 200 through the detection opening 212 when detecting the inflammable, explosive dangerous substances, thereby providing a further protection. The shielding plate 232 may be provided with an open pore 234 aligned with the detection opening 212 so that the Raman detection probe 110 is allowed to pass through the detection opening 212 and the open pore 234 that are aligned with each other so as to be located near the detection region 233, for example, located above the sample to be detected that is placed on the detection region 233. Arrangement of the aligned detection opening 212 and open pore 234 enables exactly positioning the Raman detection probe 110 near the sample to be detected after the cover 220 is closed, and thus ensures that the light beam from the Raman detection probe 110 can be irradiated onto the sample to be detected and the Raman scattering spectrum can be collected by the Raman detection probe 110 from the sample.

In another embodiment, as shown in FIGS. 2A and 2B, a probe limiting block 240 may be further provided within the detection cavity 210 and configured to guide and hold the Raman detection probe 110 passing through the detection opening 212 to be located near the detection region 233. In an example, the probe limiting block 240 may be positioned between the side wall of the detection cavity 210 in which the detection opening 212 is formed and the shielding plate 230 of the sample holder 230 in such a way that a further block of inflammable, explosive dangerous substances or gases can also be provided.

Figure 7A:
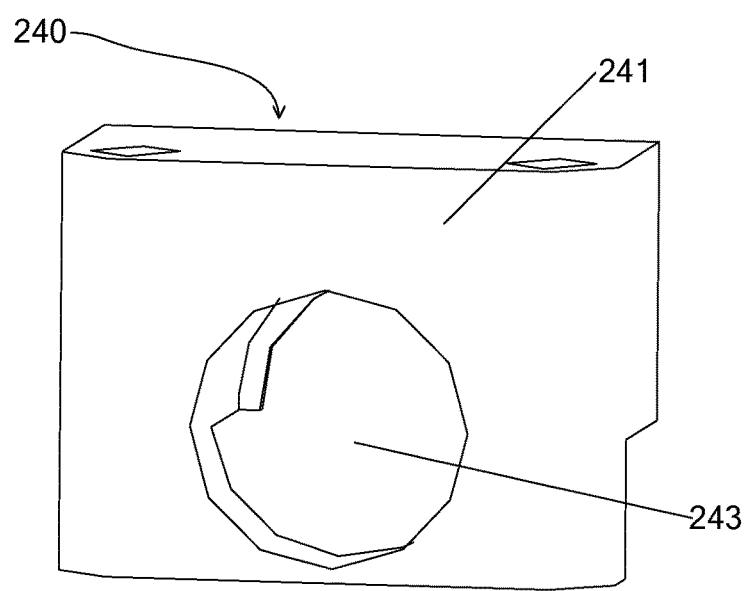
FIGS. 7A and 7B are respectively a side view and a top perspective view schematically showing a probe limiting block according to an exemplary embodiment of the present disclosure.
Figure 7B:
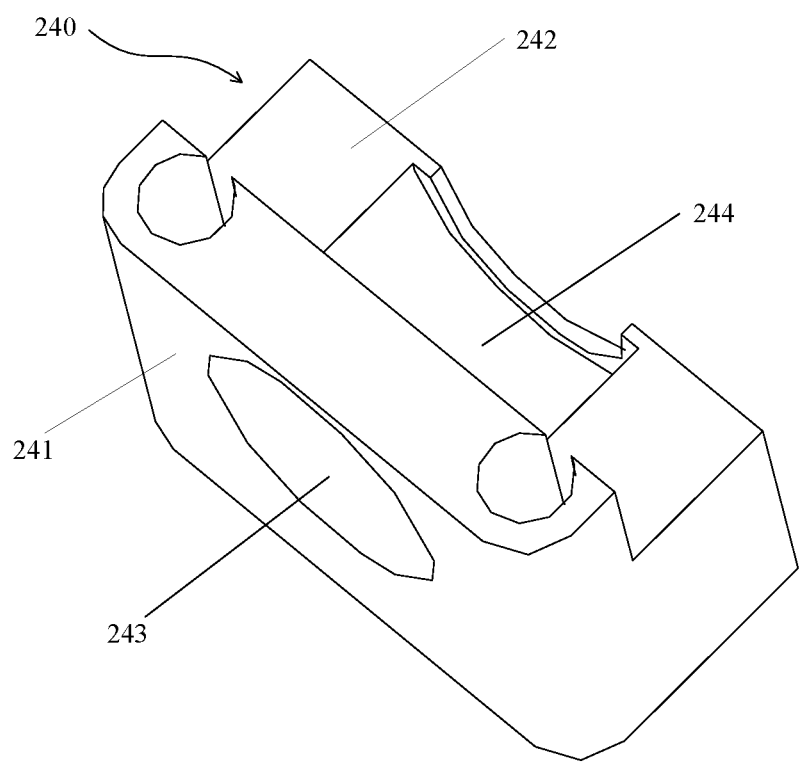

As shown in FIGS. 7A and 7B, the probe limiting block 240 may be configured, as a whole, in a substantially L-shape, which includes two portions 241 and 242 extending substantially in two directions perpendicular to each other. The vertically extending portion 241 may be provided with a limiting hole 243, which is aligned with the detection opening 212 and the open pore 234 after the probe limiting block 240 is suitably positioned within the detection cavity 210, such that the Raman detection probe 110 can pass through the detection opening 212, the limiting hole 243 and the open pore 234 that are aligned to suitably position near the detection region 233 within the detection cavity 210. The horizontally extending portion 242 of the probe limiting block 240 may be provided with a recess 244, which has a profile that is consistent with or at least conforms to at least a part of an outer profile of the Raman detection probe 110 so as to hold and limit the position of the Raman detection probe 110 within the detection cavity. The probe limiting block 240 may also be detachably or non-detachably fixed or mounted within the detection cavity 210 via various means, for example, a bolt. A quartz plate may be provided in the limiting hole 243 and/or the recess 244 of the probe limiting block, for protecting the probe. The probe limiting block may have a cylindrical, square, semi-cylindrical, conical shape or other shape, which will not be limited in the present disclosure.

In an example, the safety protection device 200 may be further provided with a pressure relief opening communication with the space, so as to release an overhigh pressure generated within the space due to deflagration and explosion of the inflammable, explosive dangerous substances during detection. Exemplarily, as shown in FIGS. 2A and 4, a pressure relief opening 215 may be provided in the side wall of the detection cavity 210, and for example, may be aligned with the detection opening 212. Of course, the pressure relief opening may be provided at other location, for example, provided in the cover 220, or provided in both the cover and the detection cavity, which will not be limited in the present disclosure. Further, a pressure relief device may be provided or mounted in the pressure relief opening, in order to prevent direct injection of high pressure hot gas.

In the present disclosure, the detection cavity 210 and the cover 220 may be engaged with each other in various ways, as long as they can be engaged to define an appropriate explosion proof container. In an embodiment, as shown in FIGS. 2A and 4, the detection cavity 210 further comprises a notched engagement ring 213 which is provided or formed at the opening end thereof and formed with a first engagement structure 214, while the cover 220 is formed with a second engagement structure 221 that is configured to be engaged with and locked with respect to the first engagement structure 214. The notched engagement ring 213 may be formed integrally with the cavity body 211 or be separately provided on the cavity body 211.

Figure 5A:
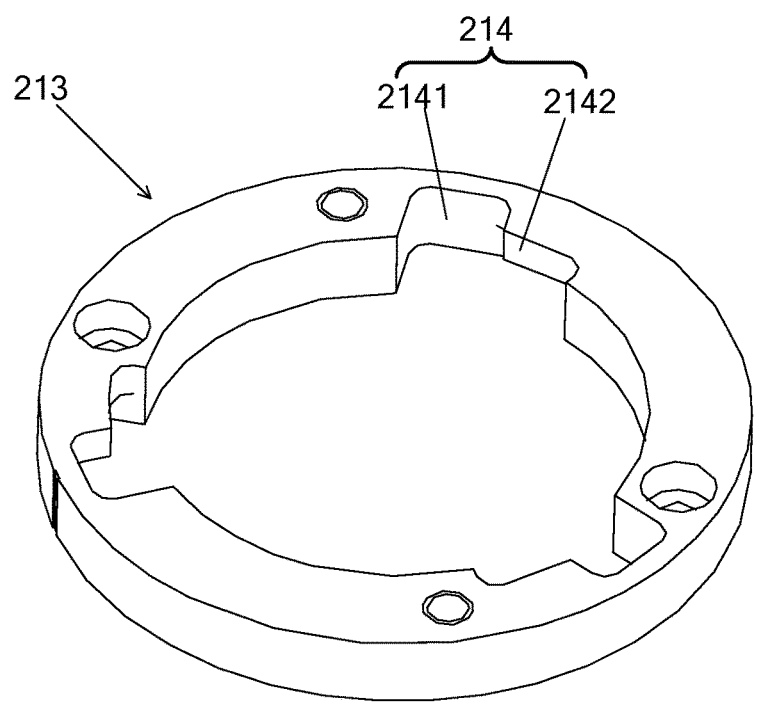
FIGS. 5A and 5B are perspective views schematically showing top and bottom of a notched engagement ring of the detection cavity shown in FIG. 4 respectively.
Figure 5B:
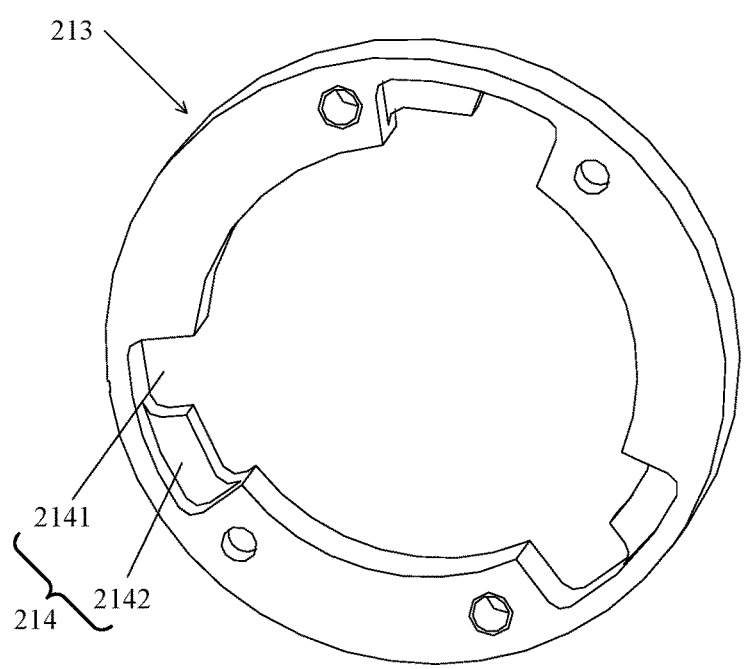

In an example, as shown in FIGS. 4-5B, the first engagement structure 214 comprises a plurality of notch engagement structures circumferentially spaced apart from each other, each notch engagement structure may comprise a notch 2141, a stop block 2142 and an engagement slot 2143 that is defined under the stop block 2142; the second engagement structure 221 may comprise a plurality of engagement legs each configured to engage a corresponding one of the notch engagement structures in a snap fit connection such that the cover 220 is detachably engaged and locked to detection cavity 210. The engagement leg formed on the cover 220 may have a substantially L-shape configuration shown in the figures, which includes a portion 2211 extending vertically downwards from a circumferential edge of an opening of the cover 220 and a portion 2212 extending substantially horizontally from the portion 2211. When the cover 220 is engaged to the detection cavity 210, the engagement leg 221 firstly enters the notch 2141 of the notch engagement structure, then the cover 220 or the detection cavity 210 is rotated such that the horizontal portion 212 of the engagement leg slides into the engagement slot 2143 defined by the stop block 2142 and is locked by the stop block 2142, thereby preventing the cover 220 from detaching from the detection cavity 210 in a vertical direction. Numbers of the notch engagement structures and the engagement legs are not limited, and a plurality of notch engagement structures and/or engagement legs may be arranged in a circumferential direction of the safety protection device, for example.

When a sample is detected by using the safety protection device provided according to the embodiments of the present disclosure, the probe limiting block and the sample holder are firstly mounted or placed within the detection cavity, then an appropriate amount of sample which, for example, may be in form of solid powder and may be loaded within a sample bag, is obtained, and the sample or the sample bag is placed at a suitable location on the sample holder; after this, the cover is closed on the detection cavity and is rotated to a closed position, and the Raman spectroscopy detection probe is inserted through detection opening into the space within the safety protection device and is brought to a position near the sample, so the detection may be started. As the detection is performed within the space inside explosion proof container formed by the safety protection device, thus even if dangerous conditions such as deflagration and explosion of inflammable, explosive dangerous substances occur during the detection, these dangerous conditions can be restricted within the explosion proof container and be effectively prevented from causing damage to a detection personnel or onsite detection operation. Further, parts of the safety protection device according to the embodiments of the present disclosure may be easily assembled and carried, enabling safe and quick detection.

It will be appreciated that although several exemplary embodiments have been shown and described, it would be appreciated by those skilled in the art that various changes or modifications may be made in these embodiments without departing from the principle and spirit of the disclosure, the scope of which is defined in the claims and their equivalents.

What is claimed is:

1. A safety protection device for Raman spectroscopy detection, comprising:
   a detection cavity comprising a cavity body, the cavity body having an opening end through which a sample to be detected is allowed to be placed into the detection cavity;
   a cover configured to cover and engage the opening end so as to form, together with the detection cavity, an explosion proof container defining a space for receiving the sample to be detected,
   a sample holder which is provided within the detection cavity and on which the sample to be detected is placed, wherein the sample holder comprises:
   a base mounted within the detection cavity and having a detection region on which the sample to be detected is to be placed; and
   a shielding plate connected with the base, the shielding plate being configured such that the detection opening and the detection region are located on opposite sides of the shielding plate and having an open pore aligned with the detection opening so that a Raman detection probe is allowed to pass through the detection opening and the open pore that are aligned with each other so as to be located near the detection region, and
   wherein the detection cavity further comprises a detection opening formed in the cavity body such that the Raman detection probe is allowed to be inserted into the space through the detection opening so as to detect the sample.

2. The safety protection device according to claim 1, further comprising a probe limiting block located within the detection cavity and configured to guide and hold the Raman detection probe that passes through the detection opening to be located near the detection region.

3. The safety protection device according to claim 2, wherein the probe limiting block comprises a limiting hole configured to be aligned with the detection opening and the open pore so as to receive the Raman detection probe.

4. The safety protection device according to claim 2, wherein the probe limiting block is positioned within the detection cavity between a side wall of the detection cavity in which the detection opening is formed and the shielding plate.

5. The safety protection device according to claim 1, wherein the detection cavity and/or the cover further comprises a pressure relief opening in communication with the space.

6. The safety protection device according to claim 1, wherein
   the detection cavity further comprises a notched engagement ring located at the opening end and formed with a first engagement structure, and
   the cover is formed with a second engagement structure configured to be engaged and locked with the first engagement structure.

7. The safety protection device according to claim 2, wherein
   the detection cavity further comprises a notched engagement ring located at the opening end and formed with a first engagement structure, and
   the cover is formed with a second engagement structure configured to be engaged and locked with the first engagement structure.

8. The safety protection device according to claim 1, wherein
   the detection cavity further comprises a notched engagement ring located at the opening end and formed with a first engagement structure, and
   the cover is formed with a second engagement structure configured to be engaged and locked with the first engagement structure.

9. The safety protection device according to claim 2, wherein
   the detection cavity further comprises a notched engagement ring located at the opening end and formed with a first engagement structure, and
   the cover is formed with a second engagement structure configured to be engaged and locked with the first engagement structure.

10. The safety protection device according to claim 3, wherein
    the detection cavity further comprises a notched engagement ring located at the opening end and formed with a first engagement structure, and
    the cover is formed with a second engagement structure configured to be engaged and locked with the first engagement structure.

11. The safety protection device according to claim 4, wherein
    the detection cavity further comprises a notched engagement ring located at the opening end and formed with a first engagement structure, and
    the cover is formed with a second engagement structure configured to be engaged and locked with the first engagement structure.

12. The safety protection device according to claim 5, wherein
    the detection cavity further comprises a notched engagement ring located at the opening end and formed with a first engagement structure, and
    the cover is formed with a second engagement structure configured to be engaged and locked with the first engagement structure.

13. The safety protection device according to claim 6, wherein the first engagement structure comprises a plurality of notch engagement structures circumferentially spaced apart from each other, and the second engagement structure comprises a plurality of engagement legs each configured to engage a corresponding one of the notch engagement structures in a snap fit connection such that the cover is detachably engaged and locked to detection cavity.

14. The safety protection device according to claim 7, wherein the first engagement structure comprises a plurality of notch engagement structures circumferentially spaced apart from each other, and the second engagement structure comprises a plurality of engagement legs each configured to engage a corresponding one of the notch engagement structures in a snap fit connection such that the cover is detachably engaged and locked to detection cavity.

15. The safety protection device according to claim 8, wherein the first engagement structure comprises a plurality of notch engagement structures circumferentially spaced apart from each other, and the second engagement structure comprises a plurality of engagement legs each configured to engage a corresponding one of the notch engagement structures in a snap fit connection such that the cover is detachably engaged and locked to detection cavity.

16. The safety protection device according to claim 9, wherein the first engagement structure comprises a plurality of notch engagement structures circumferentially spaced apart from each other, and the second engagement structure comprises a plurality of engagement legs each configured to engage a corresponding one of the notch engagement structures in a snap fit connection such that the cover is detachably engaged and locked to detection cavity.

17. The safety protection device according to claim 10, wherein the first engagement structure comprises a plurality of notch engagement structures circumferentially spaced apart from each other, and the second engagement structure comprises a plurality of engagement legs each configured to engage a corresponding one of the notch engagement structures in a snap fit connection such that the cover is detachably engaged and locked to detection cavity.

18. A Raman spectroscopy detection system, comprising:
   the safety protection device according to claim 1; and
   a detection device, the detection device comprising the Raman detection probe, which is configured to be partially inserted into the space through the detection opening and detect the sample within the space so as to obtain a Raman spectrum of the sample.

* * * * *